United States Patent [19]

Milberger et al.

[11] 4,085,121

[45] Apr. 18, 1978

[54] PREPARATION OF MALEIC ANHYDRIDE FROM FOUR-CARBON HYDROCARBONS USING TI, P, O, CONTAINING CATALYST

[75] Inventors: Ernest C. Milberger, Solon; Noel J. Bremer, Kent; Eunice K. T. Wong, Cleveland, all of Ohio

[73] Assignee: The Standard Oil Company, Cleveland, Ohio

[21] Appl. No.: 784,190

[22] Filed: Apr. 4, 1977

[51] Int. Cl.² .......................... C07D 307/60
[52] U.S. Cl. ................................ 260/346.75
[58] Field of Search ............... 260/346.75; 252/435

[56] References Cited

U.S. PATENT DOCUMENTS 2,824,073  2/1958  Rylander et al. .............. 252/435

FOREIGN PATENT DOCUMENTS 1,157,117  6/1967  United Kingdom ............ 260/346.75

*Primary Examiner*—Natalie Trousof
*Assistant Examiner*—Bernard Dentz
*Attorney, Agent, or Firm*—Gwenetta Douglas Hill; Herbert D. Knudsen; Larry W. Evans

[57] ABSTRACT

Vanadium-free catalysts consisting essentially of oxides of titanium and phosphorus have been found to be especially effective in the oxidation of n-butane, n-butenes and 1,3-butadiene with molecular oxygen in the vapor phase to yield maleic anhydride. The reaction with n-butane gives an especially pure product in good yield and selectivity.

9 Claims, No Drawings

PREPARATION OF MALEIC ANHYDRIDE FROM FOUR-CARBON HYDROCARBONS USING TI, P, O, CONTAINING CATALYST

BACKGROUND OF THE INVENTION

Maleic anhydride has been produced by the vapor phase oxidation of n-butane, n-butenes, 1,3-butadiene or mixture thereof in the presence of an oxidation catalyst. It is desired that the catalysts exhibit effective activity and high selectivity toward maleic anhydride, and various catalysts have been proposed which are based on different combinations of several components. However, those catalysts which tend to give the more desirable results generally require components which are relatively expensive, such as vanadium. For example, French Pat. No. 2287-504 to UBE Industries discloses the preparation of maleic anhydride by the catalytic vapor phase oxidation of unsaturated hydrocarbons having 4–6 carbon atoms in the presence of a catalyst containing $VP_aTi_bX_cO_d$, wherein X is at least one of Na, Ca, Mg, Fe, Zr, B, Mn, Ag or Mo; a is 1.0 to 5.0 (preferably 2–4); b is 2.0 to 12 (preferably 4.5–10); c is 0 to 1; and d satisfies the valence of the other elements present (preferably 8–40). Belgium Pat. No. 821-051 to BASF discloses the preparation of maleic anhydride by the catalytic vapor phase oxidation of linear unsaturated aliphatic hydrocarbons having 4 or more carbon atoms in the presence of a supported catalyst containing 2–25% of $V_2O_5$ (preferably 2–10)); 1–35% of $P_2O_5$ (preferably 3–25%); and 40–97% of $TiO_2$ (preferably 65–95%), the active catalytic material being 50–1500% of the support (preferably 100–600%).

British Pat. No. 1,157,117 discloses the production of maleic anhydride from a saturated aliphatic hydrocarbon having 4 carbon atoms or an unsaturated aliphatic hydrocarbon having 4 or 5 carbon atoms in the presence of a catalyst comprising an oxide of molybdenum and at least one other oxide of tin, antimony, titanium, iron or tungsten. This catalyst may optionally contain an acidic oxide of phosphorus or boron.

By the process of the present invention, the stability and activity of the catalyst are improved, and unlike most processes that involve the catalytic vapor phase oxidation of 4-C hydrocarbons to produce maleic anhydride, the catalyst composition does not require vanadium as an essential element.

SUMMARY OF THE INVENTION

It has been discovered in the process for the production of maleic anhydride by the oxidation of n-butane, n-butenes, 1,3-butadiene or mixture thereof with molecular oxygen in the vapor phase at a reaction temperature of 250° C to 600° C in the presence of a catalyst, the improvement comprising using a vanadium-free catalyst consisting essentially of the oxides of titanium and phosphorus.

The most significant aspect of the present invention is the catalyst. The catalyst may be optionally promoted with at least one element selected from the group consisting of alkali metals, alkaline earth metals, Cr, Mn, Fe, Co, Ni, Cu, Zr, Nb, Mo, Hf, Ta, W, U, Sb, Bi, rare earth elements and noble metals.

Preferred catalysts are described by the following empirical formula $Ti_aP_bO_x$ wherein a and b are 0.1 to 10;

x is the number of oxygens required to satisfy the valence states of the other elements present. Catalysts of particular interest within the formula are described wherein a and b are 0.1 to 6. Especially desirable results are observed using catalysts wherein a is 0.5 to 5 or catalysts wherein b is 0.5 to 5.

The present invention is an improved process for the production of maleic anhydride from four-carbon hydrocarbons by the use of a novel catalyst. Maleic anhydride is produced in a simple manner at a low cost utilizing inexpensive starting materials.

Catalysts of the invention may be prepared by a number of known methods. The most preferred preparation is described in the Specific Embodiments.

The catalysts may be used alone or a support could be employed. Suitable supports include silica, alumina, clay, Alundum, silicon carbide, boron phosphate, zirconia, titania, thoria, diatomaceous earth, and aluminum phosphate. The catalysts are conveniently used in a fixed-bed reactor using tablets, pellets or the like or in a fluid-bed reactor using a catalyst preferably having a particle size of less than about 300 microns. The contact time may be as low as a fraction of a second or as high as 50 seconds. The reaction may be conducted at atmospheric, superatmospheric or subatmospheric pressure.

Excellent results are obtained using a coated catalyst consisting essentially of an inert, at least partially porous support material having a diameter of at least 20 microns and an outer surface, and a continuous coating of said active catalyst on said inert support strongly adhering to the outer surface of said support. Suitable essentially inert support materials include Alundum, silican, alumina, alumina-silica, silicon carbide, titania and zirconia. Especially preferred among these supports are Alundum, silica, alumina and alumina-silica.

The catalyst may be activated by calcining it in air at a temperature of about 350° C to 700° C of a period of up to five hours or more. A preferred activation of the catalyst is accomplished by passing a mixture of steam and air or air alone over the catalyst at a temperature of about 427° C for a period of about one to five hours. The reaction temperature may vary widely and is dependent upon the particular hydrocarbon employed. Normally, temperatures of about 350° C to 500° C are preferred.

The process for preparing maleic anhydride by reacting the hydrocarbon with molecular oxygen in the vapor phase in the presence of a catalyst is known. The hydrocarbon reacted by the process of the present invention may be n-butane, n-butenes, 1,3-butadiene or mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely. The ratio of the hydrocarbon to molecular oxygen may range from about 2 to about 30 moles of oxygen per mole of hydrocarbon. Preferred oxygen ratios are about 4 to about 20 moles per mole of hydrocarbon.

SPECIFIC EMBODIMENTS

Comparative Examples A to F and Examples 1 to 10

Preparation of Maleic Anhydride Using Catalysts of Invention Compared With Use of Ti-P-V-O Catalysts A 20 cc. fixed-bed reactor was constructed on a 1.02 cm. inside diameter stainless steel tube. Catalysts prepared as described below were charged to the reactor and heated to the reaction temperature and n-butane was reacted with air in the proportions specified in the TABLE below at an apparent contact time of 1 to 4 seconds. The total usable acids were recovered and analyzed. Maleic anhydride was determined by potentiometric titration.

Comparative Examples A and B and Examples 1 and 2

The catalysts were prepared as follows:

Comparative Example A $$Ti_{1.0}P_{1.0}V_{3.7}O_x$$

A slurry was prepared consisting of 19.98 grams of titanium dioxide (Dupont), 28.69 grams of 85.4% phosphoric acid (Baker), 84.2 grams of vanadium pentoxide, and 600 mls. of distilled water. This aqueous slurry was refluxed with heating for two hours. The resulting mixture was evaporated to a thick paste, dried overnight at 110° C; calcined at 427° C for two hours; and ground and screened to 10–30 mesh.

Comparative Example B $$Ti_{1.2}P_{1.2}V_{1.0}O_x$$

This catalyst was prepared in the same manner described above using 39.95 grams of titanium dioxide, 57.38 grams of 85.4% phosphoric acid and 37.92 grams of vanadium pentoxide.

EXAMPLE 1

$$Ti_{1.0}P_{1.0}O_x$$

A slurry was prepared consisting of 39.72 grams of titanium dioxide (Dupont), 33.87 mls. of 85.4% phosphoric acid and 600 mls. of distilled water. This aqueous slurry was refluxed for three hours; boiled to a thick paste; dried overnight at 110° C; calcined at 427° C for two hours; and ground and screened to 10–30 mesh.

EXAMPLE 2

$$Ti_{3.0}P_{1.0}O_x$$

A slurry was prepared consisting of 59.92 grams of titanium dioxide (Dupont), 28.69 grams of 85.4% phosphoric acid and 600 mls. of distilled water. The resulting mixture was refluxed for two hours; evaporated to a thick paste; dried overnight at 110° C, calcined at 427° C for two hours; and ground and screened to 10–30 mesh.

Comparative Examples C to F and Examples 3 to 10

The results of the experiments in the oxidation of n-butane to produce maleic anhydride are shown in the TABLE below. The results are stated in terms of per pass conversion which is defined as Moles of maleic anhydride formed/Moles of butane fed × 100

It will be readily apparent from the TABLE that the catalysts of the invention show a maximum performance at a lower air to hydrocarbon ratio than that of the traditional P-V-O system.

In the same manner described above, catalysts of the invention may be effectively utilized in the oxidation of n-butenes and 1,3-butadiene.

Also in the same manner, various catalysts are enhanced with promoter elements to give desirable yields of maleic anhydride from n-butane, n-butenes or 1,3-butadiene.

Catalysts of the present invention may be effectively utilized in the production of phthalic anhydride from xylenes.

TABLE

| | | Preparation of Maleic Anhydride from n-Butane | | | | | |
|---|---|---|---|---|---|---|---|
| | | Temp. ° C | | Molar Feed Ratio | Contact Time | Per Pass Conversion, % | |
| Example | Catalyst | Bath | Bed | Air/n-Butane | Seconds | Total Acid | Maleic Anhydride |
| Comp. C | $Ti_{1.0}P_{1.0}V_{3.7}O_x$ | 502 | 518 | 55.2 | 1.62 | 6.1 | 5.6 |
| Comp. D | $Ti_{1.0}P_{1.0}V_{3.7}O_x$ | 479 | 492 | 56.2 | 1.67 | 9.0 | 8.7 |
| Comp. E | $Ti_{1.2}P_{1.2}V_{1.0}O_x$ | 504 | 520 | 31.7 | 2.78 | 14.9 | 14.9 |
| Comp. F | $Ti_{1.2}P_{1.2}V_{1.0}O_x$ | 483 | 499 | 31.6 | 2.81 | 14.4 | 14.4 |
| 3 | $Ti_{1.0}P_{1.0}O_x$ | 481 | 509 | 20.2 | 4.1 | 12.3 | 10.8 |
| 4 | $Ti_{1.0}P_{1.0}O_x$ | 486 | 504 | 32.2 | 2.7 | 20.2 | 19.0 |
| 5 | $Ti_{1.0}P_{1.0}O_x$ | 485 | 524 | 23.2 | 1.11 | 18.0 | 16.7 |
| 6 | $Ti_{1.0}P_{1.0}O_x$ | 504 | 524 | 32.8 | 2.61 | 19.5 | 18.3 |
| 7 | $Ti_{1.0}P_{1.0}O_x$ | 503 | 522 | 72.9 | 1.13 | 18.23 | 16.8 |
| 8 | $Ti_{3.0}P_{1.0}O_x$ | 481 | 494 | 35.0 | 2.82 | 18.8 | 16.0 |
| 9 | $Ti_{3.0}P_{1.0}O_x$ | 458 | 474 | 30.6 | 2.87 | 18.1 | 15.9 |
| 10 | $Ti_{3.0}P_{1.0}O_x$ | 430 | 443 | 30.4 | 3.0 | 14.3 | 12.1 |

We claim:
1. In the process for the production of maleic anhydride by the oxidation of n-butane, n-butenes, 1,3-butadiene or mixture thereof with molecular oxygen in the vapor phase at a reaction temperature of 250° C to 600° C in the presence of a catalyst, the improvement comprising using a vanadium-free catalyst consisting essentially of the oxides of titanium and phosphorus.
2. The process of claim 1 wherein the catalyst is described by the empirical formula

$$Ti_aP_bO_x$$

wherein a and b are 0.1 to 10;
x is the number of oxygens required to satisfy the valence states of the other elements present.
3. The process of claim 2 wherein a and b are 0.1 to 6.
4. The process of claim 2 wherein a is 0.5 to 5.
5. The process of claim 2 wherein b is 0.5 to 5.
6. The process of claim 2 wherein the reaction temperature is 350° to 500° C.
7. The process of claim 2 wherein the catalyst employed is $Ti_{1.0}P_{1.0}O_x$.
8. The process of claim 2 wherein the catalyst employed is $Ti_{3.0}P_{1.0}O_x$.
9. The process of claim 1 wherein n-butane is reacted.

* * * * *